United States Patent [19]

Roman

[11] 4,045,874
[45] Sept. 6, 1977

[54] DENTAL DRILL GUIDE ATTACHMENT

[76] Inventor: Richard C. Roman, 230 Westmoreland Drive, Vernon Hills, Ill. 60060

[21] Appl. No.: 686,716

[22] Filed: May 17, 1976

[51] Int. Cl.² .............................................. A61C 13/12
[52] U.S. Cl. .................................................... 32/40 R
[58] Field of Search ...................... 32/29, 40 R, 47, 48, 32/49; 408/110, 111, 112, 14; 77/55

[56] References Cited

U.S. PATENT DOCUMENTS

| | | | |
|---|---|---|---|
| 2,409,377 | 10/1946 | Miller | 408/112 |
| 2,792,726 | 5/1957 | Vick | 408/112 |
| 3,620,635 | 11/1971 | DalBianco | 408/112 |

*Primary Examiner*—Robert Peshock
*Attorney, Agent, or Firm*—Garrettson Ellis

[57] ABSTRACT

A drill guide attachment for dental drill handpieces and the like includes a first sleeve, and attachment means adjacent one end of the first sleeve for securing it to a dental drill positioned therein. A second sleeve is in telescoping, coaxial, sliding relation with the first sleeve and positioned adjacent the other end of the first sleeve, the sleeves being adapted for bidirectional, limited axial motion relative to each other. The second sleeve has an outer end defining a flat surface occupying a plane transverse to the major axis of the second sleeve, so that positioning of the flat surface against a work piece simultaneously positions the drill in the sleeves in a predetermined manner relative to the workpiece. The second sleeve can define aperture means for viewing the contact point between a drill positioned in the sleeves and a work piece during the drilling operation. Also, the guide attachment of this invention can be attached to the dental drill by a split ring which is forced by bevelled surface means to collapse inwardly into tight, frictional retaining contact with the housing of a drill positioned within the guide attachment.

10 Claims, 8 Drawing Figures

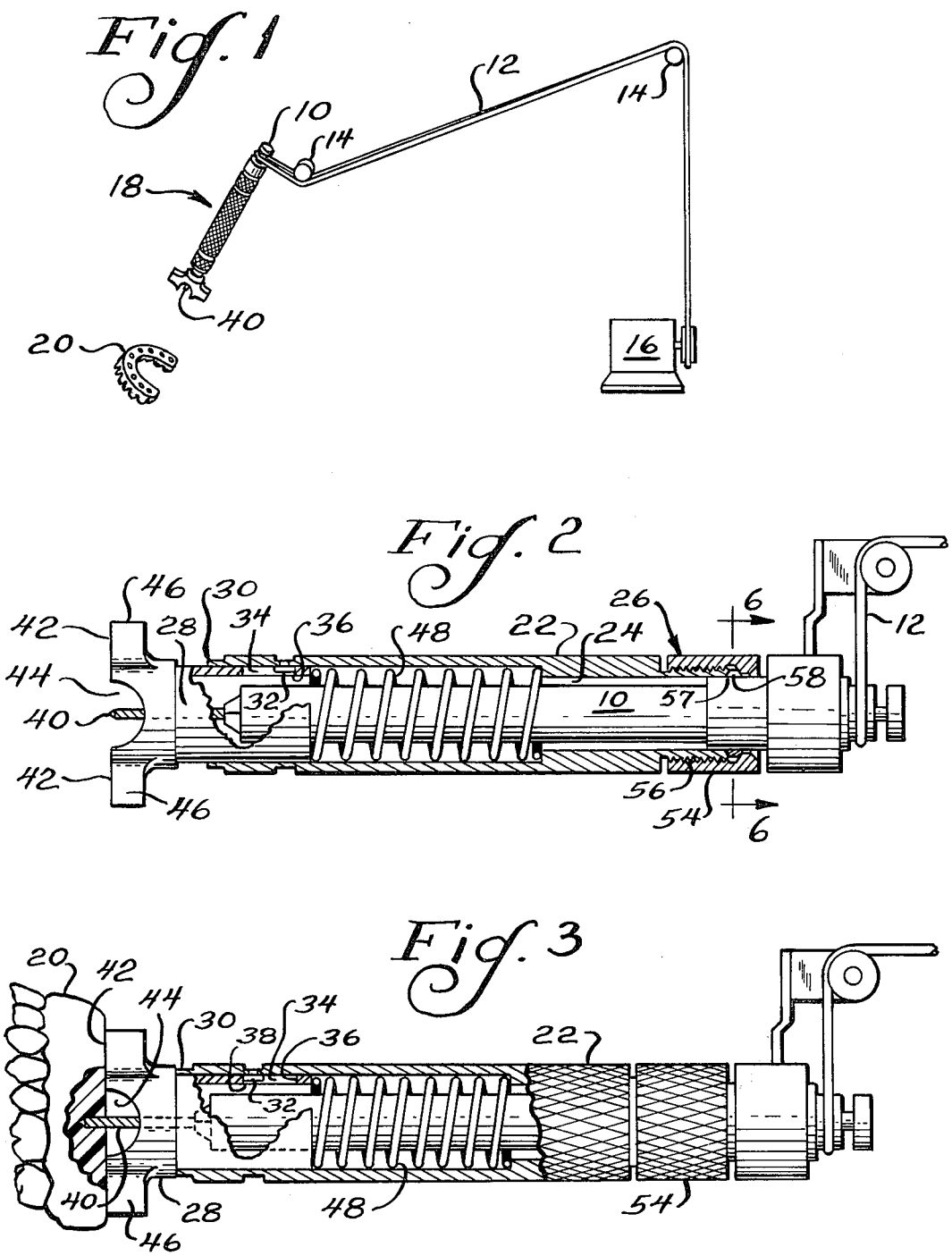

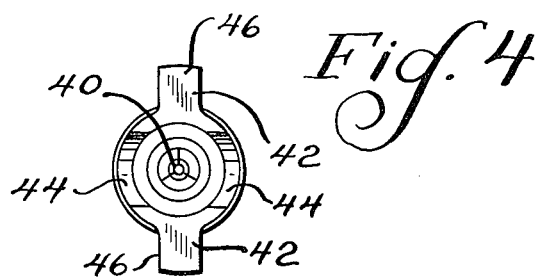
Fig. 4
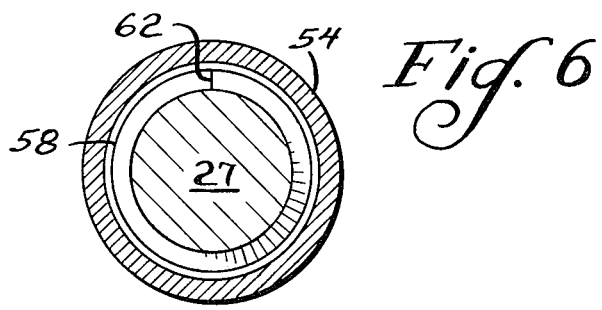
Fig. 6
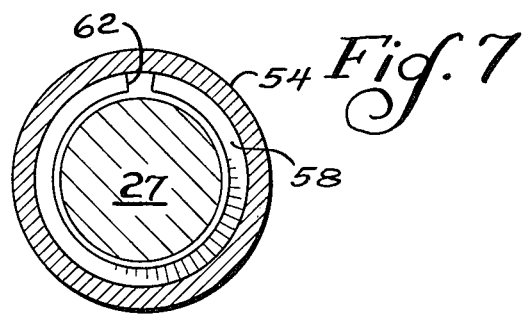
Fig. 7
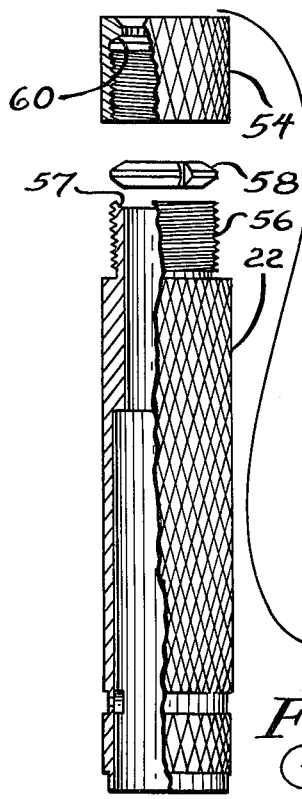
Fig. 5
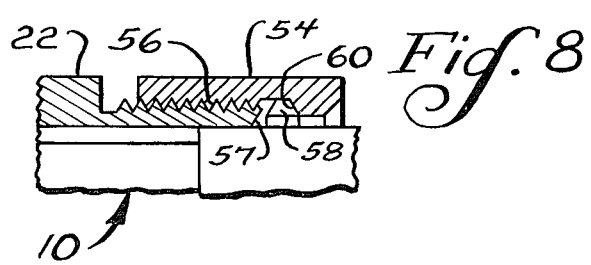
Fig. 8
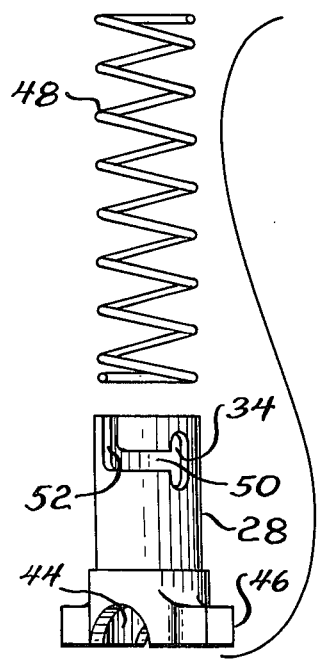

4,045,874

DENTAL DRILL GUIDE ATTACHMENT

BACKGROUND OF THE INVENTION

In the science of dentistry, die models of teeth and jaw portions are often used for making complex prosthodontic appliances, such as bridgework, crowns, and the like. This is accomplished by making an impression mold out of a quick-setting impression material around the actual teeth of a patient, thus duplicating the patient's anatomical structure. Thereafter, models of the teeth and jaw portions are reproduced from the impression, which is then utilized in the building of the dental prosthesis.

Throughout the fabrication procedure, it may become necessary to separate various portions of the model into sections. To facilitate this, several dowel pins, typically made of brass, may be inserted into the base of the die model, at least one in each area to be removed from the rest of the model.

For example, individual preparations of the model and their contacting tooth surfaces may each be penetrated from the base with one or more dowel pins. It should be noted at this point, that it is not desirable that all the die model be made to be removable. For non-removable portions, a retentive anchor is affixed to the model in the same manner as that of the dowel pins.

The model is then coated with a separating medium, and the dowel pins are encapsulated in a dental stone matrix. The model is then cut apart so that each section can be worked on independently from the rest of the model.

In preparing the die model for insertion of the dowel pins and retentive anchors, the model must first be ground to proper specifications. After this procedure, it is imperative that the holes for the dowel pins and retentive anchors be drilled at an exact angle, which is generally perpendicular to the base surface of the model. Also, the maximum depth of the hole must be a precise distance, for example ¼ inch. If the holes are drilled too deeply, or if their angular direction is other than that which was intended, the model may be ruined.

In accordance with this invention, removable drill guide attachment is provided for drills, especially dental drills, to facilitate the drilling of holes in models and the like in the precisely desired direction, for a precisely desired maximum length. Thereafter, the attachment may be removed, to permit use of the dental drill for other purposes.

DESCRIPTION OF THE INVENTION

The drill guide attachment of this invention comprises a first sleeve defining a bore adapted to receive a drill and handpiece therein. Means are provided for securing the first sleeve to a drill handpiece or housing which is positioned in the sleeve.

A second sleeve is also provided, in telescoping, coaxial, sliding relation with the first sleeve, and positioned adjacent an end of the first sleeve. The two sleeves are adapted for bidirectional, axial motion relative to each other. Also, the second sleeve has an outer end defining a flat surface which occupies a plane transverse to the axis of the second sleeve. Accordingly, positioning of the flat surface against a work piece, such as the bottom of a model, simultaneously positions the drill positioned in the sleeves in a predetermined manner relative to the work piece.

Means are provided for limiting the distance of bidirectional, axial motion between the sleeves, and resilient biasing means are provided for urging the sleeves axially apart, so that they normally reside in axially-extended position, at the limit allowed by the limiting means for their axial motion.

The second sleeve may define aperture means for viewing the contact point between a drill positioned in the sleeves, and a work piece, during the drilling operation. Accordingly, one can precisely position the drill in the attachment against the model, with the flat surface of the second sleeve also being positioned against the model. Thereafter, as the drill is advanced, the second sleeve can be pushed inwardly to facilitate this advancement, until it reaches the inner end of the permitted range of axial motion, typically a distance of about ¼ inch. Accordingly, when this inner limit of axial motion is achieved, the drill can penetrate the model no further. Hence, the drill has penetrated the precribed maximum distance permitted by the attachment of this invention, preventing the overdrilling of the holes for dowel pins and the like.

It is also contemplated, in accordance with this invention, to provide a plurality of projections carried by the second sleeve and extending outwardly therefrom, to define part of the flat surface at the outer end of the second sleeve. This facilitates the stabilization of the drill guide attachment on the model.

It is particularly preferred for a pair of such projections to be provided in diametrically opposed relation, which projections can be fit along a long, narrow section of a jaw model or the like, stabilizing the drill guide attachment as pressure is applied upon it to advance the drill. Because of the presence of these projections, the aperture means, when used in this invention, can advantageously comprise a pair of diametrically opposed, semi-circular cut-away portions at the outer end of the second sleeve, without significantly reducing the stability of the flat surface contact with the model. This facilitates observation of the contact point between the drill and the model or other work piece.

The drill guide attachment of this invention may be attached to a housing of a dental drill, positioned with it by securing means which include helical threads defined on the back end of the first sleeve, a nut member positioned on the helical threads, and a split ring positioned between the nut member and the first sleeve. Bevelled surface means are provided for forcing the split ring to collapse inwardly as the nut member is tightened on the threads. Accordingly, the split ring enters into tight, frictional retaining contact with the drill housing positioned in the sleeves. This retaining contact can of course be easily disengaged simply by loosening the nut member, for quick removal of the attachment as desired.

In the drawings, FIG. 1 is a perspective view of a typical dental drill assembly, carrying a drill guide attachment of this invention, in the process of preparing a die model of a jaw for receiving dowel pins and retentive anchors.

FIG. 2 is an elevational view, taken partly in section, of a conventional dental drill, carrying the drill guide attachment of this invention, showing the drill attachment in its normal, axially-extended position.

FIG. 3 is an elevational view similar to FIG. 2, taken partly in section, showing the drill guide attachment at the completion of drilling the undersurface of a model, in which the drill has advanced to its maximum degree, and the drill guide attachment is at its maximum axially-compressed position.

FIG. 4 is a front, elevational view of the drill guide attachment of this invention, with a drill mounted therein.

FIG. 5 is an exploded plan view of the drill guide of this invention, showing the individual parts thereof.

FIG. 6 is a transverse sectional view taken along line 6—6 of FIG. 2, showing the means for attachment of the drill guide attachment of this invention in gripping position on a drill housing.

FIG. 7 is a sectional view similar to FIG. 6 showing the attachment means in released position.

FIG. 8 is an enlarged fragmentary, longitudinal sectional view showing the attachment means in released position.

Referring to the drawings, a drill guide attachment utilizing the invention of this application is shown. A typical dental drill handpiece or housing 10 is powered by a cable loop 12 which is guided along pulleys 14 and about a motor 16.

In accordance with this invention, a drill guide attachment 18 is provided to assure the appropriate alignment of handpiece 10 against the workpiece, shown as a dental model 20 of a jaw, and to prevent overdrilling of the hole.

Drill guide attachment 18 includes a first sleeve 22, defining a bore 24, for receiving the dental handpiece 10.

A clamp system 26 is provided at one end of the first sleeve 22 (described below) is provided for securing the drill guide attachment to the handpiece 10.

A second sleeve 28 is positioned in a telescoping, coaxial sliding relation with the first sleeve and positioned adjacent an end 30 of the first sleeve. The sleeves are adapted for bidirectional axial motion relative to each other by the interaction of projection 32 on the inner wall of first sleeve 22 which normally resides in longitudinal slot 34 of second sleeve 28. As the coaxial sleeves 22, 28 extend and collapse in bidirectional axial motion relative to each other, projection 32 slides in slot 34. Bidirectional motion between the two sleeves is limited at each extreme when projection 32 comes into contact with either end of slot 34.

In FIG. 2, sleeves 22, 28 are shown in their position of maximum axial extension, where projection 32 is positioned against the inner end 36 of slot 34. In FIG. 3, sleeves 22, 28 are shown in their position of maximum axial contraction, with projection 32 positioned against the outer end 38 of slot 34.

Handpiece 10 carries a drill bit 40 which, in the axially extended position of FIG. 2, preferably has a point or tip which is essentially positioned in the plane defined by the flat surface 42 at the outer end of second sleeve 28. This flat surface is transverse to the axis of the sleeves 22, 28, and is preferably perpendicular thereto, so that handpiece 10, positioned within the sleeves, is positioned in perpendicular relation to the surface 42. Accordingly, when surface 42 is brought against a workpiece such as model 20, drill 40 is automatically positioned in perpendicular relation to the surface of model 20 to be drilled.

Spring 48, positioned in an enlarged portion of bore 24 against the back end of second sleeve 28, normally tends to bias sleeves 22, 28 into their expanded, axially-apart position.

Aperture means 44 are also provided at the outer end of second sleeve 28 to permit visualization of the junction between drill 40 and the workpiece model 20. Preferably, a pair of apertures 44 are provided, being diametrically opposed as shown in FIG. 4, and comprising semi-circular cutaway portions in sleeve 28.

A pair of projections 46 are also provided at the outer end of second sleeve 28, extending outwardly therefrom, and defining extended sections of flat surface 42. This permits the stabilization of flat face 42 on a long narrow section of the workpiece 20, even though apertures 44 are open to the workpiece 20, and thus reduce the support area of flat surface 42. The pair of apertures 44 are shown to be positioned, as in FIG. 4, on a diametric axis which is in normal relation to the diametric axis of the pair of projections 46.

Accordingly, as shown in FIG. 2, once the drill is positioned and activated, one can grip first sleeve 22 with a hand and press it toward the die model 20, to advance drill bit 40 into the model. Spring 48 is compressed, as second sleeve 28 is manually pushed into first sleeve 22. Simultaneously, drill bit 40 advances into the workpiece 20, until projection 32 strikes the outer end 38 of slot 34, at which point the inner limit of collapse of the two sleeves has been reached, and the drill bit 40 is prevented from drilling deeper into the model 20.

Accordingly, it becomes a simple matter to position the drill guide attachment in the desired place, to activate the motor, and to press the drill toward the workpiece 20. The grill guide attachment 18 resiliently collapses for the predetermined distance, while retaining the drill 40 in a desired perpendicular or other transverse relationship with workpiece 20, until the inner limit of collapse is reached. Then, the technician can know that he has drilled his hole of the desired, predetermined depth and direction, and can without further measurement or concern proceed on to the next step in his work.

Slot 34 in second sleeve 28 can communicate with a circumferential slot portion 50, also defined in second sleeve 28. Circumferential slot portion 50 joins slot 34 at an intermediate section thereof, as shown in FIG. 5.

Sleeve 28 can also define a second longitudinally disposed slot portion 52, open to the rear end of sleeve 28 and communicating with circumferential slot portion 50. Accordingly, to assemble the respective sleeves 22, 28, projection 32 may pass first through slot 52. Then the sleeves may be relatively rotated to cause the projection to pass through slot 50 into longitudinal slot 34, where it normally resides during operation as described above.

Clamp system 26 for clamping the attachment 18 to a housing 27 of a drill includes a nut member 54, having inner helical threads, mating with and positioned on corresponding outer helical threads 56 at the end of sleeve 22 as shown in FIG. 2.

A split ring 58 is positioned between nut member 54 and end 57 of the first sleeve 22. End 57 of sleeve 22 and inner annular portion 60 of nut member 54 define bevelled surfaces, as shown in FIG. 8.

Accordingly, the attachment 18 of this invention may be placed about a drill as shown in FIG. 2, with nut member 54 then being tightened on threads 56, to bring the bevelled surfaces of members 57, 60 into contact with split ring 58. Accordingly, upon further tightening of nut member 54, the bevelled surfaces force split ring 58 to move from its expanded position as shown in FIGS. 7 and 8, where the split ends of 62 of ring 58 are spaced from each other and ring 58 may be of larger inner diameter than drill housing 10, into collapsed configuration as shown in FIGS. 2 and 6, in which ends 62 of ring 58 are closer together or in contact with each other, and the inner diameter of ring 58 securely grips drill headpiece or housing 10 for clamping of attachment 18 to drill 10.

In FIGS. 6 and 7, the construction details of the sectional view taken through handpiece 10 are omitted, since they are well-known to the art and not necessary for illustrating this present invention.

When it is desired to remove attachment 18, nut member 54 is simply loosened on threads 56 so that the bevelled surfaces of the members 57 and 60 draw apart, permitting ring 58 to expand out of gripping relationship with drill 10.

The above has been offered for illustrative purposes only, and is not for the purpose of limiting the scope of this invention, which is as defined in the claims below.

That which is claimed is:

1. A drill guide attachment for dental drills and the like, which attachment comprises:
    a first sleeve defining a bore adapted to receive a dental drill therein;
    means for securing said first sleeve to a drill positioned in said first sleeve;
    a second sleeve in telescoping, coaxial, sliding relation with said first sleeve and positioned adjacent an end of said first sleeve, said sleeves being adapted for bidirectional axial motion relative to each other, said second sleeve having an outer end defining a flat surface in a plane transverse to the axis of said second sleeve, whereby the positioning of said flat surface against a workpiece simultaneously positions said drill positioned in said sleeves in a predetermined manner relative to said workpiece;
    means for limiting the distance of said bidirectional, axial motion between said sleeves;
    and resilient biasing means for urging said sleeves axially apart;
    said second sleeve defining aperture means for viewing the contact point between a drill positioned in said sleeves and a workpiece during the drilling operation;
    said flat surface at the outer end of said second sleeve being defined in part by a pair of opposed projections carried by said second sleeve and extending outwardly therefrom.

2. The drill guide attachment of claim 1 in which a pair of said projections are positioned in diametrically opposed relation.

3. The drill guide attachment of claim 2 in which said aperture means includes a pair of diametrically opposed, semi-circular cutaway portions at the outer end of said second sleeve, positioned on a diametric axis which is normal to the diametric axis of said pair of projections, said flat surface defining a plane perpendicular to the axis of said second sleeve.

4. The drill guide attachment of claim 3 in which said means for securing said sleeve to the drill comprises: helical threads defined on the end of the first sleeve; opposite to the end about which said second sleeve is positioned; a nut member positioned on said helical threads; a split ring positioned between said nut member and said one end; and bevelled surface means for forcing said split ring to collapse inwardly as said nut member is tightened on said threads, whereby said split ring enters into tight frictional retaining contact with a housing of a drill positioned within said sleeves.

5. The drill guide attachment of claim 4 in which said means for limiting the distance of said bidirectional axial motion between said sleeve comprises a projection carried by one of said sleeves, and longitudinal slot means carried by the other of said sleeves, said projection being positioned within said slot.

6. The drill guide attachment of claim 5 in which said other sleeve also defines a circumferential slot portion, communicating with an intermediate section of said longitudinal slot means, and a second, longitudinally-disposed slot portion open to an end of said other sleeve, said second slot portion communicating with said circumferential slot portion.

7. The drill guide attachment of claim 1 in which said means for limiting the distance of said bidirectional axial motion between said sleeve comprises a projection carried by one of said sleeves, and slot means carried by the other of said means, said projection being positioned within said slot.

8. A drill guide attachment for dental drills and the like, which attachment comprises:
    a first sleeve defining a bore adapted to receive a dental drill therein; means for securing said first sleeve to a dental drill, said means comprising helical threads defined on one end of the first sleeve; a nut member positioned on said helical threads; a split ring positioned between said nut member and said one end, and bevelled surface means for forcing said split ring to collapse inwardly as said nut member is tightened on said threads, to bring said split ring into tight frictional retaining contact with a housing of a drill positioned within said sleeves; and
    a second sleeve in telescoping, coaxial, sliding relation with said first sleeve and positioned about the other end of said first sleeve, said sleeves being adapted for bidirectional axial motion relative to each other, said second sleeve having an outer end defining a flat surface in a plane transverse to the axis of said second sleeve, whereby the positioning of said flat surface against a workpiece simultaneously positions said drill positioned in said sleeves in a predetermined manner relative to said workpiece;
    means for limiting the distance of said bidirectional, axial motion between said sleeves;
    and resilient biasing means for urging said sleeves axially apart.

9. A dental drill defining a drill bit and a housing, said housing carrying the drill guide attachment of claim 8, said attachment being positioned whereby said drill bit is essentially surrounded by said second sleeve while said sleeves are in their normal, axially-apart position, but said drill bit projects from said second sleeve by a predetermined distance when said sleeve is pushed axially toward said first sleeve until stopped by said limiting means of the distance of said bidirectional axial motion.

10. A dental drill defining a drill bit and a housing, said housing carrying the drill guide attachment of claim 1, said attachment being positioned whereby said drill bit is essentially surrounded by said second sleeve while said sleeves are in their normal, axially-apart position, but said drill bit projects from said second sleeve by a predetermined distance when said sleeve is pushed axially toward said first sleeve until stopped by said limiting means of the distance of said bidirectional axial motion.

* * * * *